(12) United States Patent
LaHaye (10) Patent No.: US 7,087,050 B2
(45) Date of Patent: *Aug. 8, 2006

(54) MULTI-FUNCTION SURGICAL INSTRUMENT FOR FACILITATING OPHTHALMIC LASER SURGERY

(76) Inventor: Leon C. LaHaye, 566 Sand Pit Rd., Arnaudville, LA (US) 70512

( * ) Notice: Subject to any disclaimer, the term of this patent is extended or adjusted under 35 U.S.C. 154(b) by 413 days.

This patent is subject to a terminal disclaimer.

(21) Appl. No.: 10/478,225

(22) PCT Filed: Jun. 27, 2002

(86) PCT No.: PCT/US02/20597

§ 371 (c)(1),
(2), (4) Date: Nov. 20, 2003

(87) PCT Pub. No.: WO03/002010

PCT Pub. Date: Jan. 9, 2003

(65) Prior Publication Data

US 2004/0147944 A1 Jul. 29, 2004

Related U.S. Application Data

(63) Continuation-in-part of application No. 10/071,430, filed on Feb. 8, 2002, now Pat. No. 6,656,197, which is a continuation-in-part of application No. 09/960,582, filed on Sep. 21, 2001, now Pat. No. 6,569,153, which is a continuation-in-part of application No. 09/894,264, filed on Jun. 28, 2001.

(51) Int. Cl.
A61B 18/18 (2006.01)
A61F 9/00 (2006.01)

(52) U.S. Cl. .............................. 606/4; 606/5; 606/166; 604/294; 604/300

(58) Field of Classification Search ................ 606/4–6, 606/166; 604/289, 290, 294–298, 300–316
See application file for complete search history.

(56) References Cited

U.S. PATENT DOCUMENTS 6,497,700 B1 * 12/2002 LaHaye .......................... 606/4
6,569,153 B1 *  5/2003 LaHaye .......................... 606/4
6,656,197 B1 * 12/2003 LaHaye ...................... 606/166

* cited by examiner

Primary Examiner—A. Farah
(74) Attorney, Agent, or Firm—Lemoine & Associates LLC (57) ABSTRACT

A multi-function surgical instrument for facilitating ophthalmic surgery of the eye (3) by laser means, included are a lower ring (1) and an upper ring (2). One or two intermediate rings may also be included. The lower ring (1) includes a central aperture (11) to capture the limbus and aid in positioning of the eye (3). Protuberances on the lower surface (18) of said ring (1), application of vacuum between the lower surface (18) of the ring (1) and the eye (3), or both may be used to more firmly grip the eye (3). Ports (14) disposed on the upper surface (13) of the lower ring (1) and connected to a vacuum source may be used to control hydration of the surgical field. Attached to structures of the lower ring (1) is a sterile platform (17) for reposing temporarily removed tissues (32) during the administration of laser pulses to other tissues. The upper ring (2) is disposed above the surgical bed. Ports (22) disposed along said upper ring (2) and connected to a vacuum source may be used to control smoke and splatters resulting from the ablative procedure and create additional airflow to further control hydration of the surgical field.

27 Claims, 4 Drawing Sheets

FIG. 5
(Section A-A)

FIG. 6

FIG. 7
Section B-B

MULTI-FUNCTION SURGICAL INSTRUMENT FOR FACILITATING OPHTHALMIC LASER SURGERY

This patent application is a continuation-in-part application of U.S. patent application Ser. No. 10/071,430 filed Feb. 8, 2002, now U.S. Pat. No. 6,656,197, which is a continuation-in-part application of U.S. patent application Ser. No. 09/960,582 filed Sep. 21, 2001, now U.S. Pat. No. 6,569,153, which is a continuation-in-part application of U.S. patent application Ser. No. 09/894,264 filed Jun. 28, 2001, all of which are presently pending.

1. Field of the Invention

In the field of ophthalmic surgery the use of lasers is well known. In laser assisted in-situ kerotomileusis outer tissues of the cornea are temporarily removed and pulses of laser used to remove selected portions of underlying tissue re-contouring it as desired, so that after replacement, the thickness and curvature of the cornea will have desirable changes (resulting in a desired refractory result). During such procedure, and other ophthalmic procedures involving ablation of eye tissue, the ophthalmic surgeon must address a multiplicity of issues, including positioning and fixation of the eye; placement and replacement (handling) of temporarily removed tissues; protection of the surgical bed and temporarily removed tissues from undesired laser pulses, biological and non-biological contaminants and excessive hydration or drying; control of smoke, plume or splatter; lavage, cleansing and dehydration of tissues prior to closure and closure itself, consisting of repositioning with exact alignment of tissue and finalized by promoting accelerated, uniform tissue adhesion, etc. The invention disclosed and claimed herein relates to a multi-function instrument to be placed on the surface of the eye to assist the ophthalmic surgeon in addressing these multiplicity of issues in the course of laser ablative surgery of the eye.

2. Background of the Invention

The use of lasers to reshape the cornea to obtain desired refraction changes, including by photorefractive keratectomy ("PRK") and "laser assisted in-situ kerotomileusis ("LASIK"), is well known. In such procedures precisely controlled pulses of laser light are used to remove, by ablation, thin layers of corneal tissue. In PRK the cornea is usually reshaped by first removing the epithelium and Bowman's layer (by various means) and ablating the remaining tissue by laser pulses (after which the epithelium and Bowman's layer are left to re-form by healing). In LASIK the cornea is reshaped by temporarily removing the outer layers of corneal tissue thereof by sharp instrument, ablating selected areas of the underlying tissue by laser and then replacing the temporarily removed tissues. The objective of both PRK and LASIK is to produce desirable changes in the thickness and curvature of the cornea so as to result in desirable refractive changes of the cornea. In various other ophthalmic surgery corneal tissue may be removed by ablative laser pulses. While PRK, LASIK and other ablative corneal surgeries are common procedures, with a high rate of success, a variety of complications, including development of post-surgical microstria, epithelial ingrowth and diffuse lamellar keratitis ("DLK") and infections are observed. Medical literature suggests that a majority of post-surgical complications may be avoided by meticulous surgical technique in which careful attention is paid to avoiding contamination, proper hydration, cleansing and handling of open, delicate eye tissues. At present there is no multi-function tool specifically designed with each of these objectives in mind, rather individual ophthalmic surgeons are left to improvise their own technique for accomplishing these objectives, using a plurality of instruments that a particular surgeon may select from any number of tools that were developed for other tasks, sometimes with less than desirable results. The invention disclosed herein is directed to provision of a tool specifically designed to accomplish each of these objectives in a facile and efficient manner.

In ablative surgery of the eye the ophthalmic surgeon is faced with some common challenges. Accurate positioning and fixation of the eye is important so that the laser pulses remove the desired tissue, not other tissue. As hydration of the tissues being ablated alters not only the effect of the laser on that tissue (which can result in inadequate dosage, over dosage or uneven dosage) but it also alters the size of these tissues (for instance, making refit of over-hydrated tissues temporarily removed without wrinkling, difficult or impossible); controlling hydration of both the surgical bed and temporarily removed tissues is important. It is also important to control smoke, plume and splatter not only because they may result in uneven distribution of treatment, but for other reasons relating to the health of both the patient and the surgical staff and, of course, preventing contamination, cleansing, and disinfection of open tissues is always an issue. Moreover LASIK brings with it a unique set of issues. In LASIK the outer tissues of the cornea are typically not removed entirely, but rather are left attached as a corneal "flap" by a small "hinge" of tissue. While leaving the temporarily removed tissues attached as a flap has the advantage of facilitating precise replacement of the removed tissues to their original position at the end of the procedure, the flap and its hinge must be protected from extraneous laser pulses, excessive hydration, drying and contaminants during the application of laser pulses, cleansed, properly hydrated or dehydrated and then returned to its original position at the conclusion of the procedure.

The invention disclosed and claimed herein is a multi-function surgical instrument directed to facilitating the multiplicity of above-mentioned issues which the ophthalmic surgeon must address during the course of ablative surgery of corneal tissue by laser. Facile and efficient means are provided to control positioning and fixation of the eye. Facile and efficient means are provided to isolate the surgical bed from migration of cul-de-sac liquids which may contain biological and non-biological contaminants. Facile means are provided to remove or add liquids to the surgical bed, and/or dry it by evaporative means during ablation. Facile and efficient platform means are provided upon which to repose a corneal flap away from the surgical bed and isolated from potentially contaminated cul-de-sac liquids, lashes and eye lids. Facile and efficient means are provided for evacuation of smoke, plume and splatter. Means are provided for lavage, evacuation of lavage liquids and further dehydration (by evaporative drying) of tissues prior to closure. Means are provided for facile replacement of the corneal flap to its original position for closure and further lavage and dehydration of the closed site as may be desired.

While other art discloses ophthalmic tools which include some of the features of the invention disclosed and claimed herein (for instance, smoke and plume removal), no other known art discloses a multi-function tool which is designed, or capable of, the multiplicity of issues which the invention herein discloses. The invention herein disclosed and claimed is directed to provision of a surgical instrument to facilitate the ophthalmic surgeon accomplishing the multiplicity of desirable objectives associated with laser surgery of the eye, particularly LASIK, including isolation, controlling hydration and cleansing of open tissues; storage and replacement of temporarily removed tissues; positioning and fixation of the eye; and removal of smoke, plume and splatter.

DESCRIPTION OF THE PREFERRED EMBODIMENT OF THE INVENTION

While the present invention will be described with reference to preferred embodiments, it will be understood by those skilled in the art that various changes may be made and equivalents may be substituted for elements thereof without departing from the scope of the invention. In addition, modifications may be made to adapt a particular situation or material to the teachings of the invention without departing from the essential scope thereof. It is therefore intended that the present invention not be limited to the particular embodiments disclosed herein, but that the invention will include all embodiments (and legal equivalents thereof) falling within the scope of the appended claims.

Positioning and Fixation of the Eye:

Positioning and fixation of the eye is accomplished through use of lower ring 1, in combination means for the ophthalmic surgeon to control position of the lower ring 1 itself. In the preferred embodiment lower ring 1 will be constructed of a rigid, non-toxic, non-porous and suitably inert material, which may be sterilized, such as surgical steel, titanium or polymers. In the preferred embodiment of the invention lower ring 1 is a generally ring shaped structure having an annular wall surrounding annular opening 11 therein. In the preferred embodiment of the invention the outer diameter of lower ring 1 will be sufficiently small so that lower ring 1 can be fitted to the sclera 33 of the eye without undue spreading of the lids of the eye. The area of lower ring 1 which is disposed toward the cul-de-sac tissues of the eye may have a decreased outer diameter so as to allow lower ring 1 to be fitted to sclera 33 without undue pressure on these tissues, and the area of lower ring 1 which is disposed toward the cul-de-sac tissues of the eye may be equipped with a generally horizontal shelf 131, extending the upper surface 13 of lower ring 1 radially outward, so as to hold down cul-de-sac tissues (prevent said tissues from coming into contact with upper surface 13).

In the preferred embodiment of the invention aperture 11 will be sized approximately that of the circumference of the limbus of the eye. Placed on eye 3 with the corneal bulge within aperture 11, lower ring 1 effectively "captures" the corneal bulge of the eye, which tends to restrain relative lateral movement between lower ring 1 and the eye 3.

In addition thereto, in the preferred embodiment of the invention, the lower surface 18 of lower ring 1 will be a concavely shaped surface (curving downward with increasing radius). In the preferred embodiment of the invention the curvature of lower surface 18 will generally be at least as curved as the surface of the eye outside of the limbus, or at a greater (more curved) curvature. The latter is preferred because it allows the instrument of the present invention to be facilely attached to the eye 3 by natural suction. That is, upon lower ring 1 being pressed onto the surface of the eye, the surface of the eye tends to deform into the tighter curvature of lower surface 18. Upon release of said pressure the natural elasticity of the eye tends to cause the eye to try to resume its normal curvature, causing a vacuum to be created between lower surface 18 and the surface of the eye. This vacuum attaches lower ring 1 to the surface of the eye, also tending to fix lower ring 1 in position on eye 3.

In addition to that previously described, the outer diameter of lower ring 1 may be tapered inwards (the outer diameter of lower ring 1 becoming smaller as it approaches the surface of eye 3). This tapering also aids in fixing the position of lower ring 1 on the surface of eye 3 when used in conjunction with a conventional lid speculum. A conventional lid speculum will have a superior element and an inferior element to spread, respectively, the upper and lower eyelids of the patient. By proper sizing and tapering of the outer diameter of lower ring 1, it can be "wedged" between the superior and inferior elements of the speculum. This has several advantages. Not only does wedging lower ring 1 between the speculum elements result in it more firmly being held in place, it spreads patients eyelids back farther and holds the eyelids more rigidly in place. The end result is eyelids, speculum, apparatus of the present invention and eye of the patient become all fixed firmly in place. In addition lower surface 18 of lower ring 1 may also be equipped with a set of protuberances 19 and/or external vacuum means applied between lower surface 18 and eye 3 so as to cause lower ring 1 to even more firmly grip the eye 3.

With lower ring 1 firmly fixed to the eye 3, the ophthalmic surgeon need only fix position of lower ring 1 as desired in order to fix position of the eye 3 as may be required. Various means may be employed to control position of lower ring 1. In the simplest form fixing the position of lower ring 1, thus eye 3, may be accomplished manually, the surgeon holding the instrument of the present invention in place with another instrument or by handle 4 attached to the instrument of the present invention. Alternatively, positioning of lower ring 1 may be accomplished by machine means, either by physically attaching or magnetically coupling the instrument of the present invention to a machine which either the surgeon or the laser controls. In the preferred embodiment of the invention it has been found that manual positioning by the surgeon, by means of removably (threadably) attached handle 4, which handle is also used to carry vacuum, fluid and gas sources to the present invention, is a simple, inexpensive and facile means to place the present invention on the eye, control position of the eye as desired during surgery, and remove the instrument at the completion of surgery.

Figure 1:
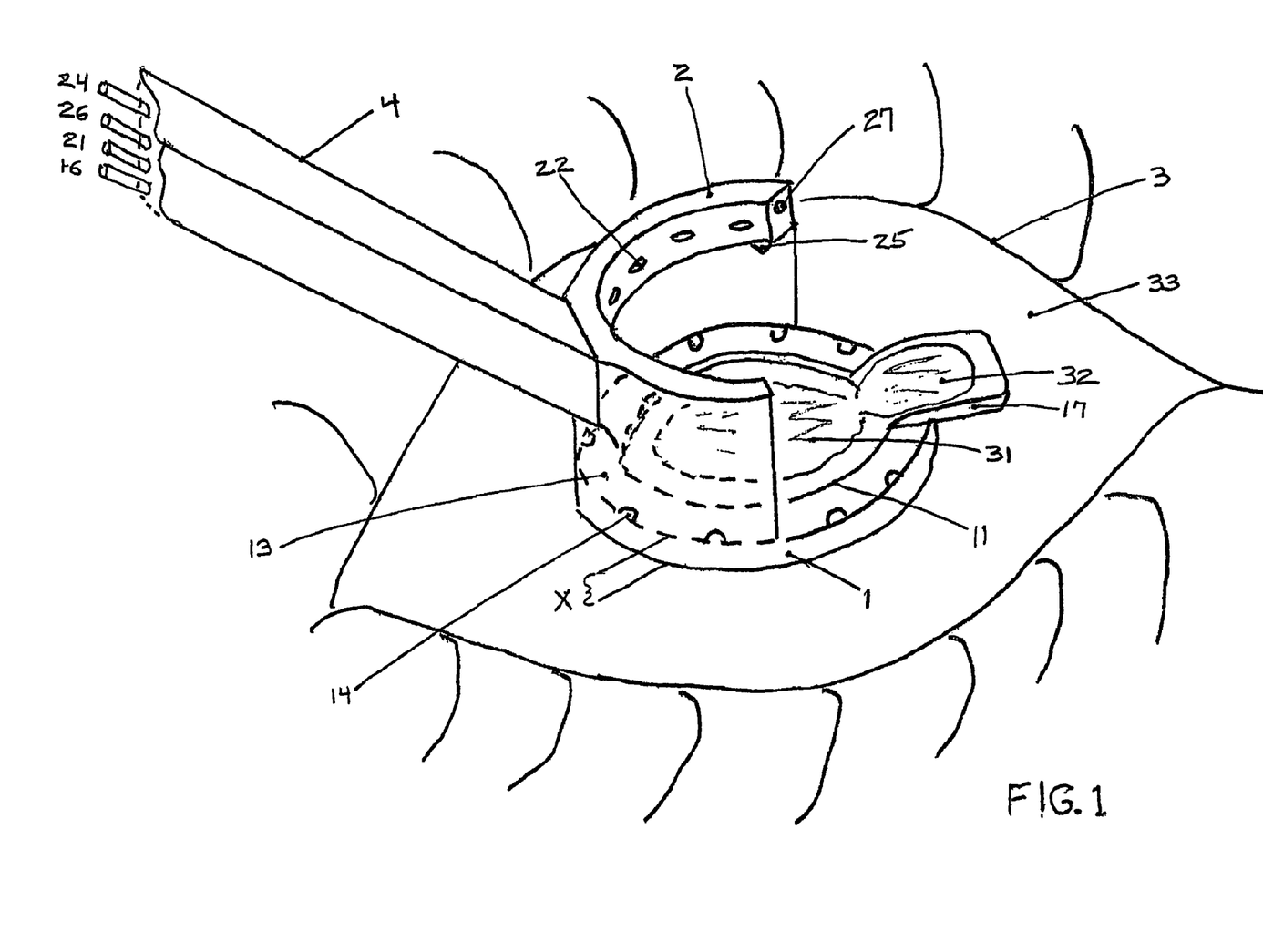
FIG. 1 is a perspective view of the preferred embodiment of the disclosed and claimed invention in the preferred, nasal, position on a patient's eye with an open stromal bed.
Figure 2:
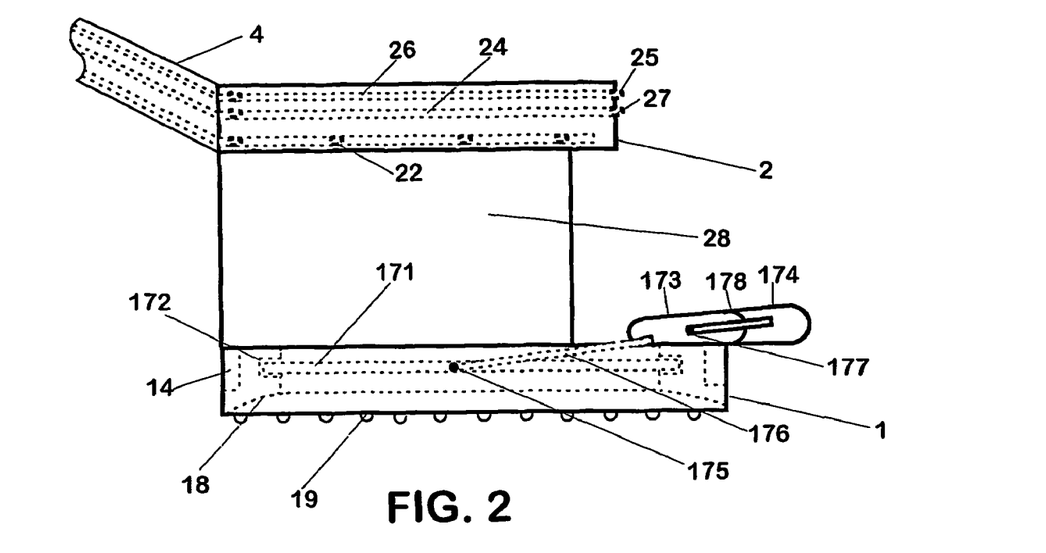
FIG. 2 is a side elevational view of an embodiment of the invention.
Figure 3:
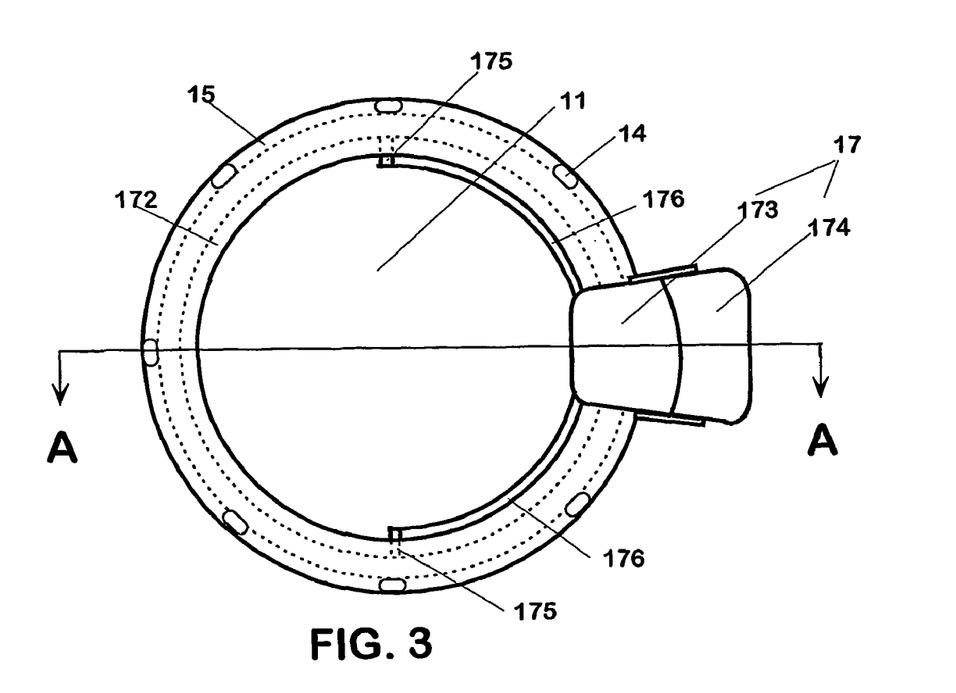
FIG. 3 is an overhead plan view of the lower ring one embodiment of the disclosed and claimed invention.
Figure 4:
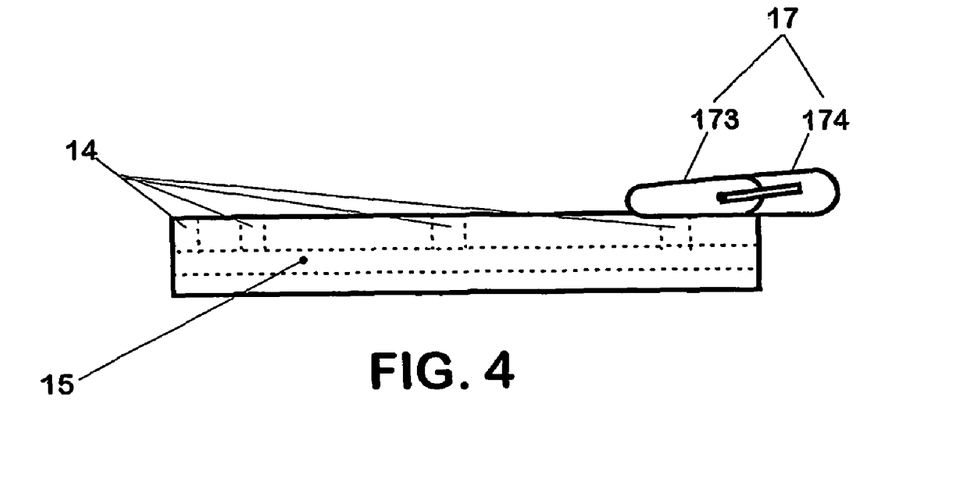
FIG. 4 is a side elevational view of the lower ring of an embodiment of the present invention.
Figure 5:
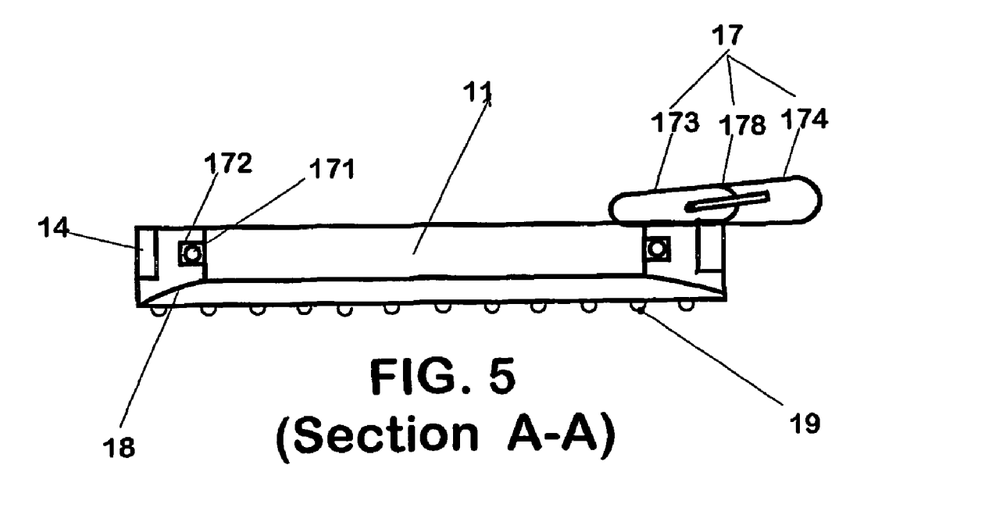
FIG. 5 is a sectional view of the lower ring of the embodiment of the invention through plane A—A of FIG. 3.
Figure 6:
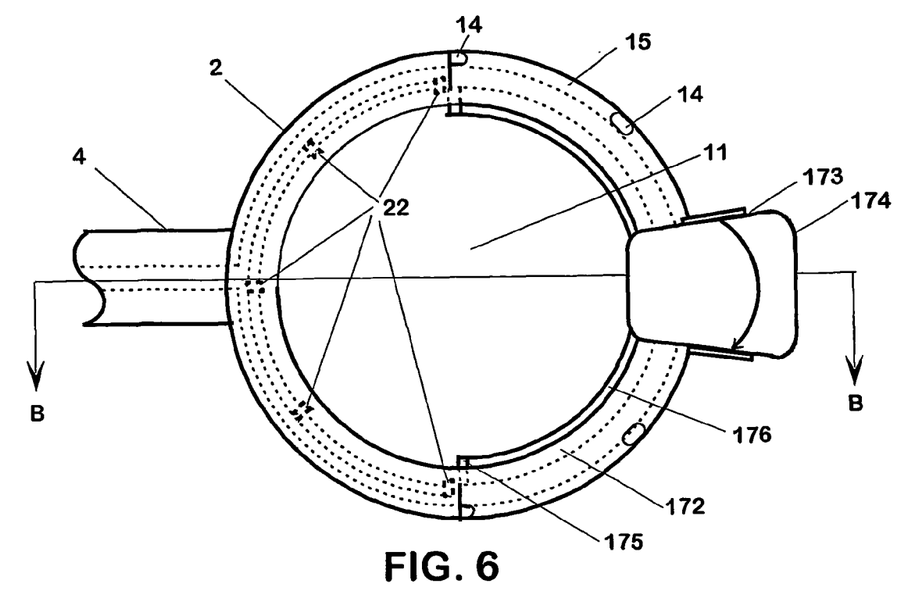
FIG. 6 is a top plan view of an embodiment of the invention (containing lower and upper rings).
Figure 7:
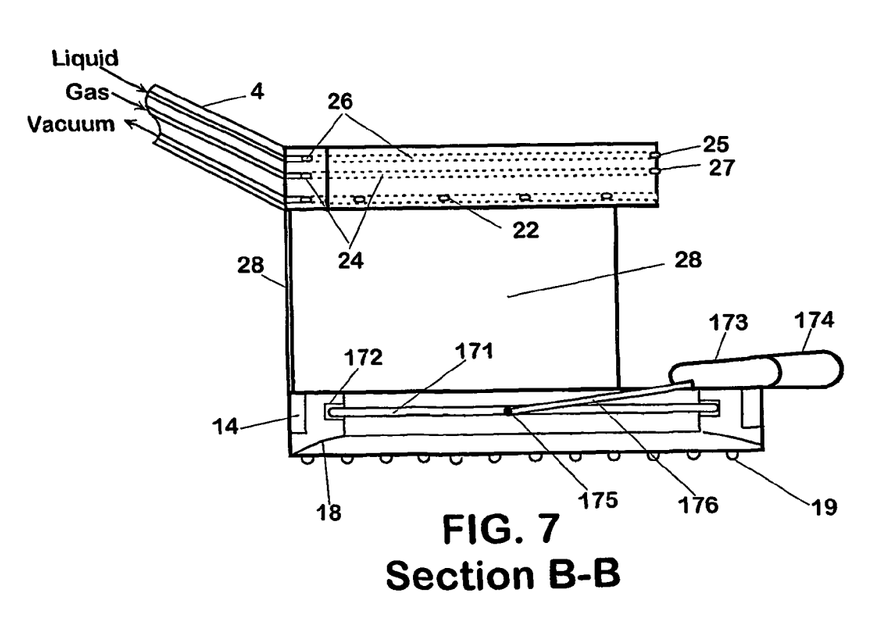
FIG. 7 is a sectional view of the lower ring of the embodiment of the invention through plane B—B of FIG. 6.

Isolation of Open Corneal Bed:

Isolation of the open corneal bed, such as stromal bed 31 of FIG. 1, is the second major function of the invention which will be discussed. Cul-de-sac liquids of the eye are known to contain various contaminants, including bacteria, sebaceous liquids, cellular debris, pyrogenic substances, chemicals, particulate matter and other substances which would be undesirable in any open wound, but particularly stromal tissue, which tissue is "spongy", can readily absorb contaminated fluids, and because of avascularity and covering of epithelial cells, infections thereof can be difficult to treat either with systemic or topical medicines. The instrument of the present invention, in particular lower ring 1 thereof, enables complete isolation of the open corneal bed, such as stromal bed 31, from cul-de-sac fluids during laser surgery of the cornea. Particular note is made of the fact that with use of the present invention the corneal bed may be, and preferably will be, completely isolated from possible contact with cul-de-sac fluids before flap 32 is lifted from stromal bed 31 until after said flap 32 is returned to cover stromal bed 31, and the now-closed wound is cleansed and antibiotics applied to the closed wound.

At least some concentric areas of the lower surface 18 of lower ring 1 will be in contact with the eye 3, sealing the eye against migration of liquids from the cul-de-sac to the area inside of aperture 11, and in particular stromal bed 31. In preference this seal is enhanced by vacuum (as described above, by pressing more curved lower surface 18 down onto the eye, and releasing said pressure, thereby causing the natural resilience of the eye to create a vacuum between lower surface 18 and the surface of the eye, or by application of an external vacuum source to lower surface 18).

Lower ring 1 also has an upper surface 13. The distance between the lower surface 18 and upper surface 13 of lower ring 1, at the outer circumference of lower ring 1, is represented by the dimension X in FIG. 1. Thus X represents the height of an annular wall which constitutes a physical barrier over which cul-de-sac fluids would have to rise before said fluids could flow onto surgical bed 31. Assuming a lid speculum is used, as is customary, part of its function is to evacuate cul-de-sac liquids, which will prevent cul-de-sac fluids from rising higher than dimension X. Even if a lid speculum is not used, or should malfunction (and cul-de-sac fluids flow onto upper surface 13 of lower ring 1) other attributes of lower ring 1 and its upper surface 13 would prevent cul-de-sac fluids from migrating onto stromal bed 31. Namely upper surface 13 is disposed at a height which is even, or preferably below stromal bed 31, tapers downward from aperture 11 and towards ports 14 (which are in communication with vacuum sources). Therefore even if cul-de-sac fluids should flow onto upper surface 13, from there they would be evacuated into ports 14 before having an opportunity to rise higher and contaminate stromal bed 31.

Furthermore in the preferred embodiment of the invention the outer diameter of upper surface 13 will have an upwardly extending lip 12. While lip 12 prevents liquids from the area within aperture 11 from flowing outward onto the sclera 33, lip 12 also provides an additional height preventing flow of liquids from the cul-de-sac onto upper surface 13 of lower ring 1, into the surgical field within aperture 11 and onto stromal bed 31. In whatever embodiment, the function of the lower ring 1 is both fixation of the eye and isolation of the surgical field, within aperture 11, from liquids external of lower ring 1, and in particular cul-de-sac liquids.

Isolation of the Corneal Flap ("Cap"):

However, in addition to these functions, in the preferred embodiment of the Invention, part of the structure of lower ring 1 has other functions, namely to serve as a sterile platform 17. In the preferred embodiment of the invention platform 17 provides not only a sterile place aside from the laser beam on which to repose flap 32, but is also structured to isolate the tissues of flap 32 from cul-de-sac liquids during surgery, and to facilitate replacement of the flap 32 over stromal bed 31 (thus "close" the surgical wound) at the conclusion of surgery.

Namely, in the preferred embodiment of the invention, lower ring 1 will have a section thereof (herein referred to as platform 17) which has an upper surface of sufficient size upon which to repose a corneal flap (sometimes called a corneal "cap"). In the preferred embodiment platform 17 will extend radially outward from aperture 11, so as to leave aperture 11 generally unobstructed, but slight extension of the platform a small distance into said aperture, so as to make the radial inward edge of the platform more coincident with the hinge 34 of flap 32, is also comprehended by the invention. In the preferred embodiment platform 17 will extend radially outward in a direction towards the medial line of the patient (nasal side of the eye as the tool is positioned on the eye), but extension of platform 17 in another direction (i.e., extending the platform superiorly, temporally, inferiorly, or otherwise), which the individual ophthalmic surgeon may prefer, is also comprehended by the invention. In any radial direction which platform 17 extends, the height of the upper surface of platform 17 of lower ring 1 will be at a height which places the upper surface of platform 17 above cul-de-sac liquids, so as to isolate flap 32 from these potentially contaminating liquids when said flap 32 is reposed on said platform 17. In the preferred embodiment the upper surface of platform 17 will also be disposed a height which is above, and is inclined toward upper surface 13 of lower ring 1. In this preferred embodiment, fluids which may splatter onto flap 32 when reposed on platform 17, or be used to rinse said flap 32, will drain onto upper surface 13 of lower ring 1, where they may be evacuated into ports 14 on said upper surface (rather than drained onto other structures of the eye). Preferably platform 17 will be constructed of a rigid, non-toxic, non-porous, non-stick and suitably inert material, which may be sterilized, such as surgical steel, titanium or polymers. Particularly its upper surface may be coated with "Teflon" or other suitably inert non-stick material. Though it is preferred that platform 17 be disposed at a height above and inclined towards upper surface 13 and be constructed of a non-porous material, disposition of the upper surface of platform 17 at the same height, or below upper surface 13 of lower ring 1, platform 17 may be flat, inclined in some other direction or a portion of it constructed of porous material, so long as the upper surface of platform 17 is elevated above cul-de-sac liquids and it is constructed of a material which will not "wick" or otherwise bring cul-de-sac fluids into contact with flap 32 when flap 32 is disposed on the upper surface of said platform.

Alignment of the Flap on Platform:

Furthermore in the preferred embodiment of the invention platform 17 has a plurality of other features to aid in proper disposition of flap 32 thereon. Namely in the preferred embodiment of the invention, platform 17 is made at least somewhat movable radially about aperture 11. This feature is desirable because hinge 34 is not always formed perfectly perpendicular to the medial line of the patient and may be skewed, and rather than adjust the position of the entire tool on the eye 3 so that the radially inward edge of platform 17 is parallel to hinge 34 (breaking the seal between lower surface 18 and the eye to move the entire tool, thereby risking contamination of the surgical field with cul-de-sac liquids), or place flap 32 onto platform 17 with hinge 34 twisted, it is better practice to move platform 17 alone so as to better align platform 17 with flap 32 and hinge 34. In the preferred embodiment of the invention platform 17 is made movable about aperture 11 by the virtue of ring-groove arrangement. Namely platform 17 is attached to a ring 171, which is slidably disposed in a groove 172 which surrounds aperture 11.

Replacement of the Corneal Flap onto the Stromal Bed:

Furthermore, In the preferred embodiment of the invention, platform 17 is structured so as to facilitate (with minimal handling) replacement of corneal flap ("cap") 32 to its original position (covering stromal bed 31) for conclusion of the surgical procedure. Namely in the preferred embodiment of the invention platform 17 will be pivotally attached to lower ring 1 (including but not necessarily limited to attachment to ring 171 within lower ring 1) along pivot axis 175, which axis will be generally parallel to hinge 34 of flap 32. This pivotal disposition enables platform 17 to be "tipped over" (inverted above) stromal bed 31. This facilitates movement of the flap 32 from platform 17 to its original position, covering stromal bed 31, for closure of the surgical wound.

While the invention comprehends disposition of pivot axis 175 various distances from hinge 34 and from a disposition radially outward therefrom to the center of aperture 11, and even somewhat beyond, in the preferred embodiment of the invention pivot axis 175 will be at least some distance radially inward (toward the center of aperture 11) from hinge 34. Therefore, disposed pivot axis 175 is "in front" of hinge 34. Thus in order for platform 17 to pivot about pivot axis 175, flap 32 must start sliding off of said platform. This is a desired result. Flap 32 is delicate and moist, and the thin corneal tissue tends to adhere (by surface tension and/or vacuum) to the upper surface (which is smooth) of platform 17 and can be difficult to "lift" therefrom without at least some risk of damage to flap 32. On the other hand, well wetted (which can be done by lavage if necessary) flap 32 can easily slide off platform 17. By disposing pivot hinge 175 "forward" of hinge 34, the more that platform 17 is "tipped over" (pivotally rotated to a position where the upper surface is inverted over stromal bed 31), the more flap 32 is slid off the platform. In practice it has been found that if the platform is tipped over quickly this will usually result in flap 32 dropping right onto stromal bed 31. In the preferred embodiment of the invention pivot arms 176 are used to extend the pivot axis of platform 17 to approximately the center of aperture 11. By use of shorter or longer pivot arms (the use of which is comprehended by the invention herein disclosed) pivot axis 175 could be moved to any other point desired.

In the preferred embodiment of the invention platform 17 has additional features which facilitate return of flap 32 to stromal bed 31 for closure of the surgical wound. Namely platform 17 may be a segmented platform. Platform 17 includes segments 173 and 174, at least one of which is (174) pivotally attached to another section (173) of platform 17. This segmentation of platform 17 (into 2 or move pivotally attached segments) provides a number of benefits. First it allows movement of the lower section of platform 17 (173) to be pivoted more than it might otherwise be (in fact nearly 180 degrees) due to various other structures of the invention on the opposite side of lower ring 1 (which may otherwise constitute obstructions to full platform movement). Also as segment 174 is pivoted "backwards" (away from the stromal bed 31), an "air gap" 178 is opened between the segments (which tends to release any vacuum which may be causing flap 32 to adhere to the upper surface of platform 17) and flap 32 is slid further off of segment 174 itself. Thus by segmenting platform 17 it can be more inverted over stromal bed 31, vacuum adhering flap 32 to the upper surface of platform 17 "broken", and the flap slid further over subsequent segments of the platform. The combined effects of all three permit the ophthalmic surgeon to easily "drop" flap 32 off of platform 17 and onto stromal bed 31 without even having to touch it with any external tool, thereby preserving sterility of flap 32 and minimizing the possibility of any "tool" damage to said flap.

In practice it has been found that the best result takes place when the segments of platform 17 are moved together as far as they will move together (which substantially inverts flap 32 over stromal bed 31, but the flap 32 remains hydraulically attached to platform 17) and then the segments of platform 17 are parted (either by pivoting segment 173 more towards the stromal bed 31, or by pivoting segment 174 away from the stromal bed 31). It is not necessary to touch the flap itself, but only the underside of the platform to do this. This almost always immediately releases flap 32 to "drop" right into position covering stromal bed 31 without any wrinkling of said flap. This is an extremely facile way to replace flap 32 over stromal bed 31 with minimal effort, without risk of damage to the flap and without the flap or stromal bed touching anything except platform 17 (which is sterile).

Aspiration of Liquids from (Dehydration of) Stromal Bed:

In addition to the above described functions and preferred structure for accomplishing said functions, in the preferred embodiment of the invention, lower ring 1 has other functions, namely removal of liquids from within aperture 11, particularly stromal bed 31. This function is desired because over-hydration of stromal bed 31 can change the effect the laser has on stromal tissue (it will generally reduce ablation resulting from a laser pulse), and thus can result In undertreatment. Moreover if the hydration is non-uniform it can result in undesired treatment results. Thus the preferred embodiment of the present invention has a variety of attributes to control hydration of the stromal bed 31, including but not limited to means of blowing a drying gas to said bed (the details of which will be disclosed later herein) and means to evacuate liquids from within aperture 11 (which will now be disclosed).

In addition to the above described functions of lower ring 1, the structure of lower ring 1 is also designed to remove liquids from within aperture 11, including stromal bed 31 disposed in said aperture. In the preferred embodiment of the invention this is accomplished by height of the upper surface 13, which may be enhanced by incline of upper surface 13 downward from aperture 11, and may be enhanced by disposition of ports 14 about upper surface 13 which are coupled to vacuum means. Namely as mentioned above, upper surface 13 is disposed at a height which is at, or below, the height of stromal bed 31, so disposed liquids on stromal bed 31 flow downward onto upper surface 13. In preference the thickness of lower ring 11 at its radially inward circumference will be as small as practical to prevent liquids from pooling at the margin between the inner circumference of lower ring 1 and the cornea. However some rounding of the radially inward circumference of lower ring 1 is desirable to prevent it from being too "sharp," possibly cutting into the corneal bulge.

In preference upper surface 13 of lower ring 1 will also be inclined downward from aperture 11, and towards ports 14 disposed about upper surface 13, so as to facilitate drainage of liquids away from aperture 11 and to ports 14. Ports 14 are connected to a vacuum source through annular passageway 15 disposed below in lower ring 1. In preference, ports 14 will also be disposed near the outer circumference of upper surface 13. This provides a practical construction of lower ring 1, which may be facilely disassembled for cleaning, sterilization or other purposes.

Pooling Desired Liquids on the Stromal Bed:

Also as mentioned above, the outer diameter of lower ring 1 may have a lip 12 extending above upper surface 13. This lip not only forms a higher barrier preventing entry of cul-de-sac liquids into the area within aperture 11, and in particular stromal bed 31, but also serves as a wall which may be used to retain desired liquids in contact with stromal bed 31. Namely upon completion of use of the laser, the ophthalmic surgeon is faced with another multiplicity of issues: removing ablative debris from the stromal bed, re-hydrating open tissues, application of medications and repositioning of the flap 32 over stromal bed 31. Lip 12 can be used (in coordination with lavage), to facilitate medication and control of whether a vacuum is applied to ports 14. Namely lip 12 permits fluids, whether medicated or not, to be pooled into contact with stromal bed 31, and then withdrawn (aspirated into ports 14 as necessary). Accordingly lip 12 will generally be at a height which is higher than stromal bed 31. This pooling not only facilitates cleansing, re-hydration and application of medicine to stromal bed 31, it has also been found particularly helpful in restoring flap 32 in correct position over stromal bed 31. Namely with liquid pooled over stromal bed 31, when flap 32 is dropped onto the stromal bed 31, flap 32 tends to try to return to its original, unwrinkled shape and "float" right into proper alignment on stromal bed 31. After the flap is floated into place the pooled liquids may be aspirated into ports 14. This tends to "seat" flap 32 in proper alignment on stromal bed 31. Only after the flap 32 is seated in place (and typically the gutter of the incision treated with topical antibiotic) is the gutter and flap gently dried with a controlled, directed flow of sterile air or sterile oxygen for the purpose of promoting accelerated, uniform sealing of flap and flap edge is the apparatus of the present invention removed. Before flap 32 was lifted from stromal bed 31 to the time flap 32 is seated back in place over stromal bed 31, it was possible with use of the invention, and such use is preferred, to have maintained isolation and sterility of all open tissues.

Plume Removal, Evaporative Dehydration and Rinsing:

The second major component of the invention disclosed and claimed herein is provided by upper ring 2. The structure of upper ring. 2 is designed to provide, or in conjunction with lower ring 1, assist with evacuation of plume, evaporative dehydration of tissues and lavage of tissues. To these ends the apparatus of the present invention is equipped with upper ring 2. Upper ring 2 is preferably constructed of a rigid, non-toxic, non-porous and suitably inert material, which may be sterilized, such as surgical steel, titanium or polymers. In general, the structure of upper ring 2 consists of at least one, and preferably a plurality (namely three) tubular structures extending about an arc generally superposed above the diameter of aperture 11. Each tubular structure has at least one and possibly a plurality of ports to accommodate the function of that individual tubular structure.

Namely tubular structure 2 is equipped with at least one, and possibly a plurality of ports 22, which in conjunction with vacuum means attached to that tubular structure, is designed to evacuate smoke, plume and splatter which results from ablation of the stromal bed 31. In the preferred embodiment upper ring 2 may be a generally circular length of rigid tubing, connected to vacuum means attached to tube 21. Ports 22 extend through the wall of said ring. While other dispositions of ports 22 is comprehended by the invention (such as ports disposed about the outer circumference, at the bottom or top of the tubing) in the preferred embodiment of the invention ports 22 are disposed facing radially inward, on the inner circumference of said tubing. Said ports may increase in size in proportion to increased distance from tube 21 in order to produce a more uniform airflow around aperture 11. Increasing intensity of the vacuum applied to the tube 21 Increases air flow and enhances removal of smoke, plume and splatter.

While upper ring 2 may constitute a full circle (such embodiment is comprehended by the invention), in the preferred embodiment upper ring 2 does not constitute a full circle, but is only a segment thereof having closed ends, which does not extend above platform 17 (so as to facilitate access to platform 17 by the surgeon).

In most cases upper ring 2 will be disposed at a height which puts vacuum ports 22 approximately 1–10 millimeters above upper surface 13 of lower ring 1. Upper ring 2 may be attached to a fixed position above aperture 11 or may be movably disposed closer or farther therefrom from aperture 11, as desired. Tubular structure 2 may also be made removably attached to any of said structures, so that the surgeon can remove it when desired.

In practice it has been found that extending a solid wall structure 28, between lower ring 1 and upper ring 2, at least to the extent that said wall structure 28 does not preclude necessary access to the eye 3 and platform 17 and allows platform 17 to be pivoted as discussed above, has a plurality of advantages. First such wall 28 tends to isolate tissues within aperture 11 from contact by various tissues of the eye, lids, eyelashes and cul-de-sac structures (caruncle, plica semi lunaris, etc.). Second said wall 28 tends to confine smoke, plume and splatter centrally, so that it may be better evacuated into ports 22. Second said wall provides a good structural member for attachment of lower ring 1 and upper ring 2 in proper relationship, and provides a convenient structural member for attachment of a handle 4, or other means to place the invention on the eye, control position of the eye, and remove the invention from the eye, to the apparatus of the present invention.

Upper ring 2 may also include one or more tubular structures 24 and ports 27 disposed therein for blowing a drying gas onto the area enclosed by aperture 11 (stromal bed 31 when the flap 32 is reposed on platform 17, or the outer surface of the flap 32 when the flap is covering the stromal bed) and/or onto platform 17 (and the underside of flap 32 when the flap is reposed on the platform). This helps prevent over-hydration of these tissue during application of laser pulses, and dry them after rinsing of these tissues. If so, used tubular structure 24 would be connected to a source of a sterile drying gas, which might be air or a gas selected for other beneficial properties, such as oxygen, etc.

Upper ring 2 may also include one or more tubular structures 26 and associated ports 25 disposed therein for dispensing a rinsing liquid onto the area enclosed by aperture 11 and/or onto platform 17. As a consequence of application of laser pulses, a certain amount of ash and other cellular debris remains on stromal bed 31 and/or is deposited on the exposed underside of flap 32. In addition, during the time said tissues are exposed, other particulate material, some of which may be biological, may accumulate on these tissues. It is suspected that these contaminants are major contributors to the post-surgical complications which do arise from laser surgery of the eye. Accordingly good practice suggests these tissues be well rinsed prior to closure. Good practice suggests that the flap 32 better aligns and adheres to stromal bed 31 if the interface between these tissues is well wetted prior to replacement of flap 32. Good practice suggests that better results are obtained if the area is well rinsed after closure, to cleanse the outer surface of the cornea, and contaminant which may be in the "gutter" of the incision. Good practice also suggests that uniform drying of the gutter and flap promotes enhanced fixation of the corneal cap as a final closing step. Thus the structure of the invention accommodates this function also. At this point it should be appreciated that only after final rinsing (which is typically followed by additional drying of the surface of the eye and application of additional antibiotic) is it necessary to remove the apparatus of the present invention. Thus from before the flap 32 was removed from stromal bed 31 at the beginning of surgery to the time the surgical wound is completely cleansed and closed, both the stromal bed 31 and the flap 32 have been in a sterile environment; smoke, plume and splatter dealt with; hydration controlled; and the tissues cleansed and facilely closed all without physical contact of the open tissues by anything except the tool of the invention, which was sterilized before commencement of the operation. Thus the tool of the present invention represents a unique and novel solution to a large number of the issues which the ophthalmic surgeon is faced with in laser surgery of the cornea.

It is thus to be appreciated that apparatus in accordance with the principles and teachings of the present inventive disclosure constitutes an advancement in the field of art to which the invention pertains. While the above description contains certain specificities, these should not be construed as limitations on the scope of the invention, but rather as an exemplification of preferred embodiments thereof. Accordingly, the scope of the present invention should be determined not by the embodiments illustrated, but by the appended claims and their legal equivalents.

What is claimed is:

1. A surgical instrument for placement around the limbus of an eye during corneal surgery thereon by laser, comprising:
   a. a lower ring having a vertical axis, an upper surface and a lower surface spaced axially apart and defining a thickness therebetween, and an outer diameter and an inner diameter spaced radially apart and defining an annular wall therebetween, all together defining a disc-shaped structure having a central aperture surrounded by an annular wall;
   b. wherein the inner diameter of said lower ring is sized to fit closely about the circumference of the limbus of the eye; and,
   c. wherein said lower ring includes a platform having an upper surface which has an area at least the size of a hinged corneal flap to be created in the course of said corneal surgery, which said upper surface of said platform extends radially outward from an inner diameter of said lower ring which is proximate to the hinge of said corneal flap and is disposed at a height which is above the lower surface of said lower ring where said lower surface of said lower ring intersects with the outer diameter of said lower ring.

2. The surgical instrument of claim 1 wherein said platform is pivotally engaged to said lower ring about a horizontal axis thereof which is disposed perpendicular to a radius of said lower ring which bisects said platform.

3. The surgical instrument of claim 2 wherein said platform is comprised of at least two segments, a first segment which is pivotally engaged to said lower ring about said horizontal axis thereof and a second segment which is pivotally engaged to said first segment about a separate axis disposed horizontally on said first segment.

4. The surgical instrument of any one of claims 1 through claim 3 wherein the central aperture of said lower ring is in communication with a drainage port which is disposed at a height no greater than the height of the corneal tissues to be treated by laser during the course of corneal surgery.

5. The surgical instrument of claim 4 wherein said upper surface of said platform is disposed at a height which is at least as high as the upper surface of said lower ring.

6. The surgical instrument of claim 4 wherein said upper surface of said platform is disposed at a height which is at least as high as the height of the corneal tissues to be treated by laser during the course of corneal surgery.

7. The surgical instrument of claim 4 wherein said lower ring includes an annular ring which is rotatably engaged to said lower ring about the vertical axis of said lower ring and said platform is pivotally engaged with said annular ring about a horizontal axis which is disposed perpendicular to a radius of said annular ring which bisects said platform.

8. The surgical instrument of claim 4 wherein said upper surface of said lower ring further comprises an annular lip which surrounds said central aperture and projects upwardly from said upper surface of said lower ring at least the height of the corneal tissues to be treated by laser during the course of corneal surgery.

9. The surgical instrument of claim 8 wherein said platform has a radially outward edge which said radially outward edge is disposed radially inward of said annular lip.

10. The surgical instrument of claim 8 wherein said lower surface of said lower ring includes an annular-shaped ring section which sealingly engages the sclera of the eye against the passage of fluids when said lower ring is disposed on said eye about the limbus thereof.

11. The surgical instrument of claim 10 wherein said platform has a radially outward edge which said radially outward edge is disposed radially inward of said annular lip.

12. The surgical instrument of claim 10 further comprising an upper arcuate structure disposed above and extending around at least a portion of said lower ring, wherein said upper arcuate structure includes a first port which is connected to external fluid source, a second port in communication with an exterior surface of said upper arcuate structure and a fluid transmissible passageway extending between said first and second ports.

13. The surgical instrument of claim 12 wherein said platform has a radially outward edge which said radially outward edge is disposed radially inward of said annular lip.

14. The surgical instrument of claim 12 further comprising a wall extending between said upper arcuate structure and the lower ring therebelow.

15. The surgical instrument of any one of claims 1, 2, 3, 8, 10, 12 or 14 wherein said upper surface of said platform is disposed at a height which is at least as high as the upper surface of said lower ring.

16. The surgical instrument of any one of claims 1, 2, 3, 8, 10, 12 or 14 wherein said upper surface of said platform is disposed at a height which is at least as high as the height of the corneal tissues to be treated by laser during the course of corneal surgery.

17. The surgical instrument of any one of claims 1, 2, 3, 8, 10, 12 or 14 wherein said lower ring includes an annular ring which is rotatably engaged to said lower ring about the vertical axis of said lower ring and said platform is pivotally engaged with said annular ring about a horizontal axis which is disposed perpendicular to a radius of said annular ring which bisects said platform.

18. The surgical instrument of claim 14 wherein said platform has a radially outward edge which said radially outward edge is disposed radially inward of said annular lip.

19. The surgical instrument of claim 4 wherein said drainage port is connected to a vacuum source.

20. The surgical instrument of claim 19 wherein said annular lip is disposed a greater radial distance from said axis of said lower ring than is said drainage port.

21. A surgical instrument for placement around the limbus of an eye during corneal surgery thereon by laser, comprising:
   a. a lower ring having a vertical axis, an upper surface and a lower surface spaced axially apart and defining a thickness therebetween, and an outer diameter and an inner diameter spaced radially apart and defining an annular wall therebetween, all together defining a disc-shaped structure having a central aperture surrounded by an annular wall;
   b. wherein the inner diameter of said lower ring is sized to fit closely about the circumference of the limbus of the eye;
   c. wherein the central aperture of said lower ring is in communication with a drainage port disposed at a height which is no greater than the height of the corneal tissues to be treated by laser during the course of corneal surgery;
   d. wherein said upper surface further comprises an annular lip which surrounds said central aperture and projects upwardly from said upper surface at least the height of the corneal tissues to be treated by laser during the course of corneal surgery; and,
   e. wherein said lower surface of said lower ring includes an annular shaped ring section which sealingly engages the sclera of the eye against the passage of fluids when said lower ring is disposed on said eye about the limbus thereof.

22. The surgical instrument of any one of claims 8, 10, 12, 14 or 21 wherein said drainage port is connected to a vacuum source.

23. The surgical instrument of claim 22 wherein said annular lip is disposed a greater radial distance from said axis of said lower ring than is said drainage port.

24. The surgical instrument of any one of claims 8, 10, 12, 14, 21 or 19 further comprising an upper arcuate structure disposed above and extending around at least a portion of said lower ring, wherein said upper arcuate structure includes a first port which is connected to an external fluid source, a second port in communication with an exterior surface of said upper arcuate structure and a fluid transmissible passageway extending between said first and second ports.

25. The surgical instrument of claim 24 further comprising a wall extending between said upper arcuate structure and the lower ring therebelow.

26. The surgical instrument of claim 12 or 24 wherein said upper arcuate structure is comprised of a plurality of fluid transmissible passageways, each of which said passageways includes a first port which is connected to an external fluid source and a second port in communication with an exterior surface of said upper arcuate structure.

27. Tho surgical instrument of claim 10 or 21 wherein said annular-shaped ring section is concavely curved to conform to the curvature of the eye which is outside of the circumference of the limbus thereof.

* * * * *